United States Patent [19]

Whittle

[11] 4,364,945

[45] * Dec. 21, 1982

[54] NASAL COMPOSITION FOR RELIEVING NASAL DISTRESS

[76] Inventor: Barry J. Whittle, 8770 Sand Point Way NE., Seattle, Wash. 98115

[*] Notice: The portion of the term of this patent subsequent to May 26, 1998, has been disclaimed.

[21] Appl. No.: 255,360

[22] Filed: Apr. 20, 1981

Related U.S. Application Data

[63] Continuation of Ser. No. 103,208, Dec. 13, 1979, Pat. No. 4,269,835.

[51] Int. Cl.$^3$ ............... A61K 31/54; A61K 31/355
[52] U.S. Cl. .................... 424/247; 424/250; 424/263; 424/267; 424/273 B; 424/273 R; 424/274; 424/283; 424/284; 424/330
[58] Field of Search ............ 424/247, 250, 263, 267, 424/273 B, 273 R, 274, 283, 284, 330

[56] References Cited

U.S. PATENT DOCUMENTS

| | | | |
|---|---|---|---|
| 3,803,179 | 4/1974 | Ahrens | 424/284 X |
| 3,825,563 | 7/1974 | Ahrens | 424/284 X |
| 4,269,835 | 5/1981 | Whittle | 424/247 |

OTHER PUBLICATIONS

Handbook of Non-Prescription Drugs, 5th Ed., 1977, pp. 110 & 111.

*Primary Examiner*—Leonard Schenkman
*Attorney, Agent, or Firm*—Seed, Berry, Vernon & Baynham

[57] ABSTRACT

A nasal composition is disclosed for relieving nasal distress of a cold which does not employ a vasoconstrictor compound. The nasal composition, administered preferably in atomized form into the nasal passages, consist of a buffered, isotonic, aqueous solution containing from 0.25 to 0.8 by weight of an antihistamine compound in combination with one or more isomers of vitamin E, such as, the maleate or succinate esters of alpha, beta, gamma, delta or epsilon tocopherols.

1 Claim, No Drawings

NASAL COMPOSITION FOR RELIEVING NASAL DISTRESS

This is a continuation of application Ser. No. 103,208, filed Dec. 13, 1979 now U.S. Pat. No. 4,269,835.

BACKGROUND OF THE INVENTION

1. Field of the Invention

This invention relates to a nasal composition administered generally in atomized formed and useful without a vasoconstrictor compound for relieving nasal distress.

2. Prior Art Relating to the Disclosure

The nasal compositions generally available commonly contain one or more anithistamine compunds combined with a vasocontrictor compound such as epinephrine or neosynephrine. The action of the vasoconstrictor compound is counter to that of the antihistamines in that the vasoconstrictor compound, on contact with the membranes lining the nasal passages, constricts the blood capillary vessels and surrounding membranes to shrink and open the nasal passages. Because of this constriction, optimum action of the anithistamine in reducing fluid discharge from the nasal passage membranes is restricted. Further, once the effect of the vasoconstrictor compound wears off, the membranes lining the nasal passages tend to swell to a greater extent than previously, with resulting greater nasal congestion. Repeated use of such nasal sprays over a prolonged period of time results in severe nasal congestion and nasal distress.

SUMMARY OF THE INVENTION

It is a primary object of this invention to provide a composition for relieving nasal distress caused by allergic reaction consisting essentially of a buffered isotonic, aqueous solution containing from 0.25 to 0.8% by weight of an antihistamine in combination with one or more isomers of vitamin E, the composition not inhibiting the action of the antihistamine, increasing the biological activity of and soothing the cellular membranes lining the nasal passages.

These and other objects are accomplished by providing a nasal composition which contains a buffered isotonic aqueous solution which does not contain a vasoconstrictor compound as a decongestant and which contains only an antihistamine in an amount ranging from 0.2 to 0.8 percent by weight, in combination with one or more isomers of vitamin E.

DESCRIPTION OF THE PREFERRED EMBODIMENTS

An aqueous, buffered isotonic solution of an antihistamine without a vasoconstrictor compound is preferably employed, with the solution containing from 0.25 to 0.8% by weight of the antihistamine. The buffer may be a salt of weak acid and a stong base such as sodium borate or sodium phosphate dissolved in the aqueous solution with the antihistamines. The antihistamine employed in the composition may be any one or more of the many known antihistamine compounds, the antihistamine present in the composition in an effective amount to restrict the production of histamines by the cells lining the nasal passages, generally from 0.25 to 0.8% by weight. The antihistamine compounds which may be used include chlorpheniramine maleate, antazoline phosphate, bromodiphenhydramine hydrochloride, brompheniramine maleate, carbinoxamine maleate, chlorcyclizine HCl, chlorothen citrate, clemizole HCl, cromolyn sodium, dexchlorpheniramine maleate, diphenhydramine HCl, diphenylpyraline HCl, doxylamine succinate, methapyrilene fumarate, methapyrilene HCl, methdilazine, methdilazine HCl, phenindamine tartrate, promethazine HCl, pyrilamine maleate, pyrrobutamine phosphate, rotoxamine tartrate, trimeprazine tartrate, tripelennamine citrate, tripelennamine HCl, triprolidine HCl, and chlorpheniramine gluconate. Chlorpheniramine maleate, present in an amount ranging from 0.25 to 0.5% by weight is preferably used.

In combination with the antihistamine, one or more of the isomers of vitamin E is included. The vitamin E compound may be in a form of one or more of the natural or synthetic isomers of tocopherol or the acid esters of the alpha, beta, gamma, delta or epsilon tocopherols such as d-alpha tocopheryl acid succinate, d-alpha tocopheryl sodium succinate, d-alpha tocopheryl acetate, dl-alpha tocopheryl acetate or succinate, d-alpha tocopherol, dl-alpha tocopherol, beta tocopherol, gamma tocopherol, delta tocopherol, or epsilon tocopherol. It has been noted that the use of such compounds in combination with an antihistamine in a nasal composition of the type described does not inhibit the action of the antihistamine as does the use of the vasoconstrictor compounds. Additionally the use of such vitamin E compounds increases the biological activity of the composition, appears to sooth the nasal passages, and provides membrane stability.

It may be necessary to add an emulsifier for the vitamin E compound to the aqueous solution containing the antihistamine to aid in holding the vitamin E compound in solution. The emulsifying agents may be glycerine, for example. The amount of international units of the vitamin E compound added should be the maximum amount which can be retained in solution in the composition.

The composition is applied topically to the nasal passages, preferably in the form of an atomized spray. Even though the composition does not employ a decongestant, topical application of the composition to the nasal passage linings relieves nasal congestion without inhibiting the action of the antihistamine compound.

The following composition was forumulated for treatment of hay fever and nasal allergy problems.

| COMPOUNDS | |
|---|---|
| Chlorpheniramine maleate | 0.5% by weight |
| Sodium Borate | 0.16% by weight |
| D-alpha tocopheryl succinate | (saturated solution thereof) |
| Benzalkonium chloride | 1 part to 15,000 parts solution |
| Distilled water | 100 mls. |

Because of the absence of a decongestant or sympathomimetic compound, the composition allows the antihistamine to quickly penetrate into the nasal membranes and associated capillary network.

I claim:

1. A composition for topical application to the nasal passageways which does not employ a vasoconstrictor compound as a decongestant, consisting essentially of a buffered, isotonic aqueous solution containing an effective amount of antihistamine and a saturated amount of one or more of the natural or synthetic isomers of tocopherol or the esters of one of the isomers of tocopherol.

* * * * *